United States Patent
DeMeo et al.

(10) Patent No.: US 8,691,136 B2
(45) Date of Patent: *Apr. 8, 2014

(54) ORIENTED POLYMER IMPLANTABLE DEVICE AND PROCESS FOR MAKING SAME

(75) Inventors: Joseph DeMeo, Newtown Square, PA (US); Patrick E. Heam, Aston, PA (US); Robert L. McDade, Downingtown, PA (US)

(73) Assignee: Kensey Nash Corporation, Exton, PA (US)

( * ) Notice: Subject to any disclaimer, the term of this patent is extended or adjusted under 35 U.S.C. 154(b) by 1151 days.

This patent is subject to a terminal disclaimer.

(21) Appl. No.: 12/119,959

(22) Filed: May 13, 2008

(65) Prior Publication Data

US 2008/0228187 A1 Sep. 18, 2008

Related U.S. Application Data (63) Continuation of application No. 10/780,159, filed on Feb. 17, 2004, now Pat. No. 7,378,144.

(51) Int. Cl.
*B29C 43/00* (2006.01)
*B29C 43/02* (2006.01)
*B29C 43/16* (2006.01)
*B32B 7/02* (2006.01)

(52) U.S. Cl.
USPC ........... 264/322; 264/162; 264/299; 264/319; 264/320; 264/323; 264/325; 264/327; 264/330; 264/331.11; 264/331.21; 264/334; 428/212; 428/364; 428/397; 428/399

(58) Field of Classification Search
None
See application file for complete search history.

(56) References Cited

U.S. PATENT DOCUMENTS

| | | | |
|---|---|---|---|
| 3,161,709 A | 12/1964 | Noether et al. | |
| 3,422,181 A | 1/1969 | Chirgwin, Jr. | |
| 4,091,057 A * | 5/1978 | Weber | 264/2.2 |
| 4,282,277 A | 8/1981 | Austen et al. | |
| 4,463,753 A * | 8/1984 | Gustilo | 606/308 |
| 4,743,257 A | 5/1988 | Tormala et al. | |
| 4,874,564 A * | 10/1989 | Sudani et al. | 264/29.7 |
| 4,968,317 A | 11/1990 | Tormala et al. | |
| 5,007,818 A * | 4/1991 | Barancik et al. | 425/144 |
| 5,169,587 A | 12/1992 | Courval | |
| 5,427,731 A * | 6/1995 | Chesna et al. | 264/327 |
| 5,431,652 A | 7/1995 | Shimamoto et al. | |
| 5,492,452 A * | 2/1996 | Kirsch et al. | 411/455 |
| 5,674,286 A | 10/1997 | D'Alessio et al. | |
| 5,792,400 A | 8/1998 | Talja et al. | |
| 5,824,247 A | 10/1998 | Tunc | |
| 5,827,287 A | 10/1998 | Tunc | |
| 5,981,619 A * | 11/1999 | Shikinami et al. | 523/113 |
| 6,007,539 A * | 12/1999 | Kirsch et al. | 606/75 |
| 6,053,214 A * | 4/2000 | Sjoberg et al. | 138/134 |
| 6,168,626 B1 | 1/2001 | Hyon et al. | |
| 6,206,883 B1 | 3/2001 | Tunc | |
| 6,221,075 B1 | 4/2001 | Tormala et al. | |

(Continued)

*Primary Examiner* — Vivian Chen
(74) *Attorney, Agent, or Firm* — Jeffrey R. Ramberg (57) ABSTRACT

A device is formed by the process into a bone screw or fastener, wherein the head has a degree of polymer alignment and strength, and wherein the shank has a higher degree of polymer alignment and strength. In practice of the present invention, the polymer slug is pressed into the die cavity by the actuation of ram press, causing the slug to conform to the die cavity. Through this process, the polymer molecular orientation is aligned to different degrees, in different zones of the device.

11 Claims, 5 Drawing Sheets

(56) References Cited

U.S. PATENT DOCUMENTS

| | | |
|---|---|---|
| 6,228,111 B1 | 5/2001 | Tormala et al. |
| 6,232,384 B1 | 5/2001 | Hyon |
| 6,281,262 B1 * | 8/2001 | Shikinami ............... 523/105 |
| 6,383,187 B2 | 5/2002 | Tormala et al. |
| 6,406,498 B1 | 6/2002 | Tormala et al. |
| 6,494,704 B1 * | 12/2002 | Andersen et al. ............ 425/258 |
| 6,503,278 B1 | 1/2003 | Pohjonen et al. |
| 6,511,511 B1 | 1/2003 | Slivka et al. |
| 6,551,343 B1 * | 4/2003 | Tormala et al. ............ 606/213 |
| 6,632,503 B1 * | 10/2003 | Shikinami et al. ............ 428/131 |
| 6,803,443 B1 * | 10/2004 | Ariga et al. ............ 528/354 |
| 6,905,501 B2 * | 6/2005 | Nakamura et al. ............ 606/301 |
| 7,378,144 B2 * | 5/2008 | DeMeo et al. ............ 428/212 |
| 2001/0004693 A1 | 6/2001 | Burkhead et al. |
| 2001/0031966 A1 | 10/2001 | Tormala et al. |
| 2003/0006533 A1 | 1/2003 | Shikinami et al. |
| 2003/0146541 A1 | 8/2003 | Nakamura et al. |
| 2003/0222380 A1 * | 12/2003 | Katzir ............ 264/667 |
| 2010/0191292 A1 * | 7/2010 | DeMeo et al. ............ 606/301 |
| 2010/0305712 A1 * | 12/2010 | Ringeisen et al. ............ 623/23.5 |

* cited by examiner

ORIENTED POLYMER IMPLANTABLE DEVICE AND PROCESS FOR MAKING SAME

CROSS-REFERENCE TO RELATED APPLICATIONS

This patent document is a Continuation of commonly owned U.S. patent application Ser. No. 10/780,159, filed Feb. 17, 2004, U.S. Pat. No. 7,378,144, in the names of Joseph DeMeo et al. and entitled, "Oriented Polymer Implantable Device and Process For Making Same." The entire content of the prior application is expressly incorporated by reference.

BACKGROUND OF THE INVENTION

This application relates generally to medical implant devices and their production, specifically relating to the process of manufacturing a polymer tissue and/or bone fixation device, preferably made of a resorbable polymer. The invention more particularly concerns a method of manufacturing a resorbable bone fixation device (e.g., screw, rod, pin, etc.) by forcing a provided polymer slug or billet into a mold while the polymer is in a glass transition state, wherein the manufacturing process creates a near final shape of varying diameter and zones with variable degrees of alignment of the polymeric molecular structure and tailored mechanical properties (e.g., higher strength).

Common techniques utilized in the past for the production of shaped polymer materials have included, machining (e.g. milling, turning, etc.), injection molding, and extrusion. Machining a desired shape from a generic slug or billet often results in excessive waste, as the amount of material that is trimmed or cut off in making the final product will be much greater than the amount removed during final machining of a molded or formed polymer material that is shaped nearly to final form. For example, in machining a screw shape, having a head and a threaded body portion, from a slug or billet in the shape of a cylinder, material must be removed to arrive at the diameter of the head. Subsequently, more material must be removed to arrive at the desired diameter for the threaded body portion. This extensive machining creates a great amount of chips or cut dust as waste of the material that is machined off.

Excessive waste of raw material is especially problematic in devices constructed of relatively expensive polymers, such as bioabsorbable polymers and medical grade polymers, as costs are elevated due to the loss of the material, or additional costs are incurred in recapturing and recycling the material. A need exists for a manufacturing technique that results in higher productivity and higher yield than machining.

Injection molding is a process in which a polymer is heated to a highly plastic state and forced to flow under high pressure filling a mold cavity, where it solidifies. Melt molding processes result in a material having a relaxed orientation or molecular arrangement of the polymer as it cools, and typically does not impart great strength values, such as those required for tissue and/or bone fixation treatments suitable for implantation through surgical techniques (e.g., orthopedic and traumatology applications).

It has long been known that the production of a polymer material having an aligned orientation (i.e., not relaxed) of the polymer molecules or structure typically results in a stronger material. This correlation has been discussed in the prior art, for example see U.S. Pat. Nos. 3,161,709; 3,422,181; 4,282,277; 4,968,317; and 5,169,587, where it is described that polymer materials may be drawn or extruded to cause the orientation of a semi-crystalline or crystalline polymer structure to become substantially aligned, thereby increasing the mechanical strength of the material.

As discussed in U.S. Pat. No. 4,968,317 issued to Tormala et al., the prior art of using melt molding techniques such as injection molding and extrusion to make resorbable polymer implants results in strength values that are typical of thermoplastic polymers. It is known that the strength and modulus values may be increased by creating a reinforced composite (i.e., incorporating reinforcing fibers), however to achieve satisfactorily large strength values with reinforced composites as implants, the implant must necessarily be large in order to accommodate the stresses placed upon it.

As is known, and is further described by Tormala et al., a technique for the processing of polymer material may utilize mechanical deformation, such as drawing or hydrostatic extrusion, to alter the orientation of the molecular structure of crystalline structure and amorphous structure to a fibrillar state, in order to yield higher strength and elastic modulus values. Tormala et al. describe drawing the material through the extrusion process, resulting in an extruded material that is at least partially fibrillated as the polymer molecules and molecular segments are aligned along the drawing direction. Tormala et al. in U.S. Pat. No. 6,383,187 describe a resorbable screw made of the material described in the U.S. Pat. No. 4,968,317 patent. A need exists for a fibrillar material that may be created in varying cross-sections and diameters, in order to minimize the amount of machining required to finish the product. A further need exists for an implantable device having variable states or degrees of alignment of the polymer molecules. This may be accomplished by manufacturing or processing a material that is formed to final part geometry or near final part geometry of a device or implant, thereby reducing the need for final machining, and also obtaining increased mechanical strengths for implant applications.

In U.S. Patent Application 2003/0146541, Nakamura et al. describe a press molding process for the manufacture of a resorbable polymer bone-joining device having molecular orientation. The described process requires imparting the existing molecular orientation, preferably by stretching the primary article along the long axis, then providing the oriented primary article for press molding of the screw head and shank threads. The press molding as applied to the polymer material allows the molecular orientation of the primary article to be substantially maintained. Nakamura et al. do not describe a process for creating a device having variable cross section and variable states of alignment of the polymer molecules, wherein the process of manufacturing the areas with varying cross-sections imparts an increased orientation of the polymer molecules.

In U.S. Patent Application 2003/0006533, Shikinami et al. disclose a twice-forged resorbable polymer material, wherein the polymer molecular orientation is altered by each of the forging processes to create "orientation along a large number of reference axes having different axial directions". The forging steps applied to the polymer result in the orientation of the polymer molecules to create a room temperature flexible material, capable of withstanding repeated bending without breaking. U.S. Patent Application 2003/0006533 does not describe a polymer material that is shaped into varied cross-sections and possessing varied zones of polymer orientation.

In U.S. Pat. No. 6,232,384, Hyon discloses a resorbable bone fixation material comprising a resorbable polymer, hydroxyapatite and an alkaline inorganic compound, wherein the bone fixation material is made by the process of providing a melt with the aforementioned components, molecularly orienting the melt through a molding or extension process and extending and orienting the chain molecules of the polymer.

Preferably the molding process is performed through ram or hydrostatic extrusion. Hyon does not describe an implantable material having varied cross-section and varied zones of polymer orientation.

In U.S. Pat. No. 6,503,278, Pohjonen et al. disclose an implantable surgical device made from a resorbable, non-crystalline (i.e., amorphous) polymer. The amorphous material described by Pohjonen et al. is molecularly oriented and reinforced by mechanical deformation. Pohjonen et al. do not describe a polymer implant material having zones of variable states of alignment of the polymer molecules and varying cross section of the material.

In U.S. Pat. No. 5,431,652, Shimamoto et al. disclose a high strength polymer material that is hydrostatically extruded through a die under pressure to reduce voids and to form a resorbable polymer material that retains at least 85% of its strength after 90 days implantation. The material described in the Shimamoto et al. patent does not result in a polymer implant material or implant with complex geometry or variable shape other than the cross section of the die exit, nor does Shimamoto et al. arrive at or describe variable states of alignment of the polymer molecules.

In U.S. Pat. No. 6,511,511, Slivka et al. disclose a polymer implant that is either porous or non-porous, where the material has been reinforced by the addition of oriented fibers. The Slivka devices are made by precipitating the polymer out from a solvent solvating the polymer. The precipitation of the polymer causes a gel formation, which may then be handled and placed in a mold. Slivka et al. do not describe a polymer implant having variable shape and variable states of alignment of the polymer molecules.

The prior art described does not disclose a polymer implantable device having an orientation of the polymer molecules, wherein the shaping process creates zones of varying cross section and orientation.

It is the intent of this invention to overcome these and other shortcomings of the prior art.

SUMMARY OF THE INVENTION

It is an object of this invention to provide a shaped polymer article having sufficient strength to serve as an implantable tissue or bone fixation device.

It is another object of the invention to provide a method of manufacturing the implantable device by a process that results in varying zones of polymer orientation. The degree of polymer orientation has a correlation with the physical properties (e.g., strength, elasticity, etc.) of the material. Higher strength may be achieved by providing higher degree of polymer orientation.

In one embodiment, a polymer slug is driven into a die cavity tooling to form an implantable device, having varied cross section and varied degree of polymer orientation.

In a preferred embodiment of the process, the device is formed into a bone screw or fastener, wherein the head has a degree of polymer alignment and strength, and wherein the shank has a higher degree of polymer alignment and strength.

The process of practicing the present invention (as will be further explained), in its basic form, involves the steps of:
a) providing a polymer slug, die cavity tooling, and ram press, wherein said die cavity tooling defines a die shape;
b) placing said polymer slug between said ram press and die cavity tooling;
c) actuating said ram press in order to apply pressure upon said slug, thereby forcing said slug to conform to said die shape, wherein said slug is formed into a device comprising zones of variable alignment of the polymer structure, and zones of varying cross-section;
d) removing said device from said die cavity tooling; and optionally,
e) shaping the device to the finished product, the shaping may be performed by a machining procedure, a compression molding procedure or other techniques known in the art.

DETAILED DESCRIPTION OF PREFERRED EMBODIMENTS

The present invention consists of a method for producing a surgical polymer implant, such as a tissue fixation device, or a bone fixation or treating device. The implant may be formed in any shape suitable for implantation into the living being and may be fastened into or onto tissue or bone (e.g. a screw, pin, rod, nail, plate, staple, suture anchor or in the form of a similar type fastener or related component.) In the preferred embodiment, the bone treating device or implant processed through the method described in the present invention consists of a bioabsorbable polymeric material or matrix. In an alternative embodiment, the polymeric material of the implant may be non-resorbable. The polymer may feature a semi-crystalline, crystalline or amorphous structure. A semi-crystalline or crystalline structure polymer material features an arrangement of the polymer molecules in three-dimensional spherulitic structures and may further feature lamellae, a folded crystalline structure. The amorphous polymer structure generally lacks the lamellae found in the crystalline and semi-crystalline polymer structures. The polymer matrix material may be composed of a polymer; alternatively the material may comprise a copolymer or a mixture thereof.

The preferred, and most widely used bioabsorbable polymers to be processed through the application of this invention consist of poly(lactic acid) or PLA, poly(glycolic acid) or PGA, their copolymers and stereocopolymers such as poly (glycolide-co-L-lactide) or PGA/PLLA, or Poly-DL-lactide (DLPLA), but are not limited to these preferred or widely used materials. Other resorbable and non-resorbable polymer materials may be suitable for practicing this invention. Examples of resorbable polymers that can be used to form the device are shown in following Table 1. These materials are only representative of the materials and combinations of materials, which can be used in the practice of the current invention.

TABLE 1

Examples of Bioresorbable Polymers for Construction of the Device of the Current Invention Aliphatic polyesters
Bioglass
Cellulose
Chitin
Collagen
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
Modified proteins
Nylon-2
PHBA/γ-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β-hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly(Amino Acids)
Starch
Trimethylene carbonate (TMC)
Tyrosine based polymers The appropriate polymer matrix or material to be processed in practicing the present invention may be determined by several factors including, but not limited to, the desired mechanical and material properties, the surgical application for which the implant device is being produced, and the desired degradation rate of the device in its final application.

The previously mentioned polymeric materials may also be compounded with one or more additive materials. The additive materials may serve various functions, including, but not limited to, serving to reinforce the polymer matrix material, and serving to deliver therapy or beneficial agents to the body. Examples of reinforcing additive materials include ceramics (e.g., hydroxyapatite, tricalcium phosphate (TCP), etc.), fibrous materials (e.g., fibers, whiskers, threads, yarns, meshes, nets, weaves, etc.), or particulates (e.g., microspheres, microparticles, beads, etc.) In those embodiments where at least one fibrous reinforcement is incorporated, the reinforcing fiber may be in any suitable form (e.g., chopped, short, long, continuous, individual, bundled, weaved, etc.) The reinforcing additive material may be comprised of similar or different material than the polymer matrix material. Suitable reinforcement material may include the previously mentioned and most widely used bioabsorbable polymers, the resorbable polymers of Table 1 above, their copolymers and their stereocopolymers, as well as reinforcement materials such as ceramics, metals and bioactive glasses and their compounds. Reinforcement material may be non-bioabsorbable material, and may also be used in conjunction with a bioabsorbable polymer matrix material and be processed through the method of the present invention to form a bone-treating device. Other non-limiting examples of suitable materials that may be added to the polymer material are listed in Table 2.

TABLE 2

Reinforcing Materials suitable for use in the Present Invention

Alginate
Calcium
Calcium Phosphate
Ceramics
Chitosan
Cyanoacrylate
Collagen
Dacron
Demineralized bone
Elastin
Fibrin
Gelatin
Glass
Gold
Hyaluronic acid
Hydrogels
Hydroxy apatite
Hydroxyethyl methacrylate
Hyaluronic Acid
Nitinol
Oxidized regenerated cellulose
Phosphate glasses
Polyethylene glycol
Polyester
Polysaccharides
Polyvinyl alcohol
Radiopacifiers
Salts
Silicone
Silk
Steel (e.g. Stainless Steel)
Synthetic polymers
Titanium The additive materials may also comprise biologically active agents (e.g., therapeutics, beneficial agents, drugs, etc.) that are delivered to the living being upon implantation of the device. The additive material may comprise a substance that serves to encourage tissue ingrowth into the device (e.g., TCP, hydroxyapatite, etc.) The additive materials may also serve as a drug delivery mechanism, wherein a biologically active agent is coated onto or mixed with the polymeric material. Alternatively, the biologically active agent may be coated onto or contained within other additive material that is then added to the polymer. The therapy delivery may occur rapidly once implanted (as in the case of a surface coating), or alternatively, longer-term drug delivery is contemplated and may be achieved, where the drug delivery occurs for all or a portion of the duration of the implant's degradation. Examples of biologically active agents that may be delivered in the device are shown in following Table 3. These materials are only representative of the classes or groups of materials and combinations of materials, which can be used in the practice of the current invention, although some specific examples are given.

TABLE 3

Examples of Biological Active Ingredients

Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
    GP IIb-IIIa inhibitors
        eptifibatide
Anti-proliferation agents
    Rho Kinase Inhibitors
        (+)-trans-4-(1-aminoethyl)-1-(4-pyridylcarbamoyl)
        cyclohexane
Anti-rejection agents
    Rapamycin
Anti-restenosis agents
    Adenosine $A_{2A}$ receptor agonists
Antisense
Antispasm agents
    Lidocaine
    Nitroglycerin
    Nicarpidine
Anti-thrombogenic agents
    Argatroban
    Fondaparinux
    Hirudin
    GP IIb/IIIa inhibitors
Anti-viral drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)

TABLE 3-continued

Examples of Biological Active Ingredients vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (VPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
inflammatory mediator
Insulin
Interleukins
Interlukin-8 (IL-8)
Interlukins
Lipid lowering agents
Lipo-proteins
Low-molecular weight heparin
Lymphocites
Lysine
MAC-1
Methylation inhibitors
Morphogens
Nitric oxide (NO)
Nucleotides
Peptides
Polyphenol
PR39
Proteins
Prostaglandins

TABLE 3-continued

Examples of Biological Active Ingredients

Proteoglycans
    Perlecan
Radioactive materials
    Iodine - 125
    Iodine - 131
    Iridium - 192
    Palladium 103
Radio-pharmaceuticals
Secondary Messengers
    Ceramide
Somatomedins
Statins
Stem Cells
Steroids
Thrombin
Thrombin inhibitor
Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus The inclusion of groups and subgroups in Table 3 is exemplary and for convenience only. The grouping does not indicate a preferred use or limitation on use of any drug therein. That is, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include both forms.

The additive materials may also comprise plasticizers or other materials to provide desirable application properties to the final implant device. Plasticizers or materials that enhance the malleability of the material may allow the processing of the material of the present invention to occur at lower temperatures, providing various benefits (e.g., reduced polymer and additive material breakdown, reduced cooling times, reduced costs, increased productivity, increased polymer chain alignment, etc.).

The following description with reference to the associated figures describes the features of the present invention, wherein like numbers refer to like components.

Figure 1:
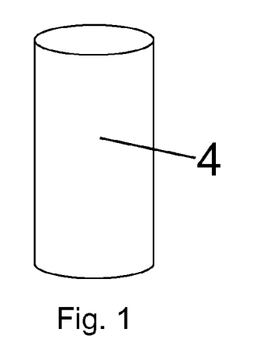
FIG. 1: Depiction of cylindrical polymer slug, billet, or blank suitable for use in the present invention.
Figure 2A:
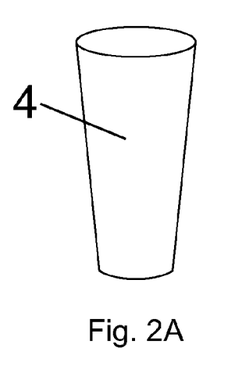
FIGS. 2A and 2B: Depictions of alternate shapes of polymer slugs, billets, or blanks.
Figure 2B:
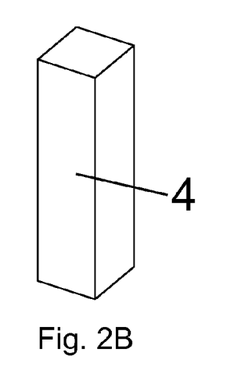

The present invention consists of a method for producing a surgical implant, such as a tissue fixation device, or a bone-treating device, which begins with a provided mass of polymer material called a slug or billet of determinate length. With reference to FIGS. 1, 2A and 2B, the slug of material 4 may be provided having an initial shape or geometry. Preferably, the slug 4 is provided in a simple cylindrical form as shown in FIG. 1, although the slug may be provided in other general shapes, for example, as shown by the alternative slug configurations depicted in FIGS. 2A and 2B.

Figure 3A:
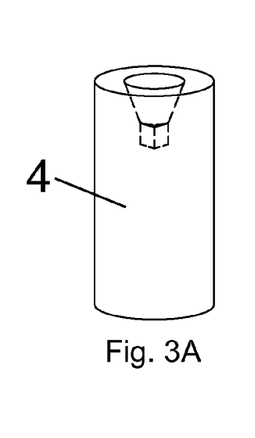
FIGS. 3A and 3B: Depictions of polymer slugs, billets, or blanks having complex internal (3A) or external (3B) geometry.
Figure 3B:
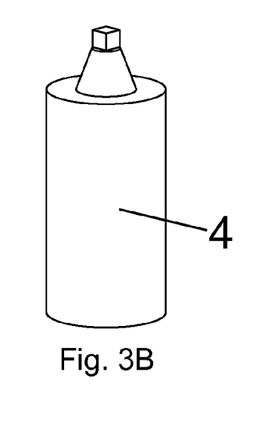

As can be seen in FIGS. 3A and 3B, the slug 4 may also be provided having a section of more complex geometry, internally and/or externally of the predominate general slug shape. This complex geometry included in the slug may take on the form of geometry that is indicative of the final bone treating device or implant, as can be seen in FIGS. 3A and B. FIG. 3B depicts an example of complex external geometry on a predominately simple cylindrical slug, while FIG. 3A depicts an example of complex internal geometry on a similar cylindrical slug. The complex geometry may be any additional formation than would occur with a general shaped slug in a simple shape (e.g., cylinder, box, conical, etc.)

The complex geometry may be incorporated into the slug through typical melt processing techniques such as injection molding or through traditional machining techniques or alternatively through the method of this present invention. The complex geometries shown in FIGS. 3A and 3B may be final device geometry that is maintained throughout the processing method of the device and such complex geometry in this example could be used as the interface between the final device and the surgical instrument, a driver of a fastener for example. Complex geometry is not limited to the designs shown in FIGS. 3A and 3B, but particular to the geometry of the final implant or device and the extent of feasibility with the processing method described in the present invention.

The slug or billet 4 is described as having a determinate length in that the length and subsequent mass of the slug has been determined and based on the final implant, tissue fixation device or bone treating device to result from the method and tooling utilized and described in the present invention.

The raw material for the provided slug material can be processed and formed through standard manufacturing techniques known in the art, including, but not limited to, traditional melt processes for thermoplastics (e.g., injection molding, single screw extrusion, twin screw extrusion, compression molding, etc., and combinations thereof), as well as through the method of this present invention. Techniques utilized for manufacturing a slug may impart orientation to the polymer structure, as has been discussed earlier, with reference to U.S. Pat. No. 4,968,317. The creation or increase of orientation in the polymer structure results in a stronger material, relative to a similar polymer material lacking equivalent orientation. The preferred material for the provided slug will have at least some orientation, such as a polymer slug material that has been processed through an extrusion process, which inherently creates a degree of molecular orientation. An alternate embodiment may provide a semi or randomly oriented polymer slug material, such as that resulting from injection molding, which offers limited preferred orientation and is heavily dependant upon tooling design and process conditions. However, melt processes not resulting in highly oriented material, such as injection molding, offer advantages that may be necessary in terms of incorporating complex geometry in the slug as shown in FIGS. 3A and 3B. The provided slug material may also be machined to desired geometry and/or tolerances through typical machining techniques following initial typical melt processing. Independent of the degree of molecular orientation of the beginning slug or the method used for fabricating the beginning slug, the final material or device formed by the method of the present invention will result in improved orientation in comparison to the originally provided slug or billet.

The material of the provided slug is processed through the practice of the present invention to arrive at the final desired implant, tissue fixation device or bone treating device, therefore, any additive materials added to the provided polymer slug are incorporated into the final product of the invention. For example, a fiber reinforced slug results in a fiber reinforced implantable device, similarly, a slug incorporating drug therapy measures will result in an implant incorporating drug therapy measures.

Figure 4A:
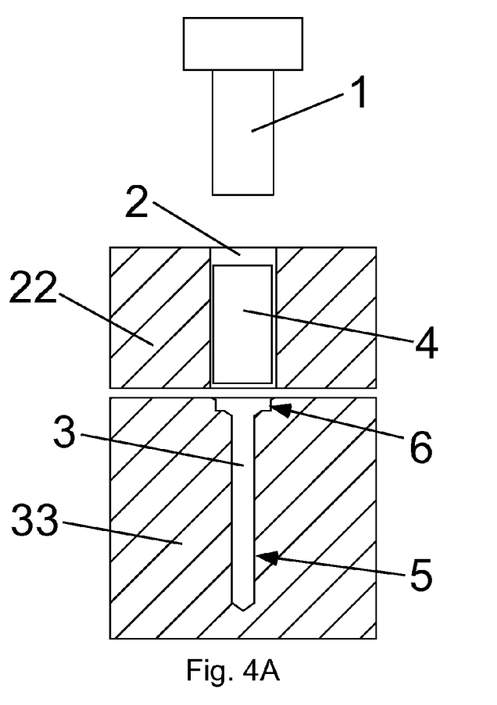
FIGS. 4A and 4B: Cross sectional depictions of die tooling arrangements suitable for use in the present invention.

With reference to FIG. 4A, the preferred arrangement of the tooling used for the method of the present invention includes a press ram 1, a barrel 2 or similar holding and/or heating chamber as defined by barrel tooling 22, and a die cavity 3 defined by die cavity tooling 33. The slug 4 is placed in the barrel portion 2 of the barrel tooling 22. The barrel tooling 22 may be a separate component that has been affixed to the die cavity tooling 33 or alternatively may be an integral one-piece design comprising both the barrel tooling 22 and the die cavity tooling 33.

Figure 4B:
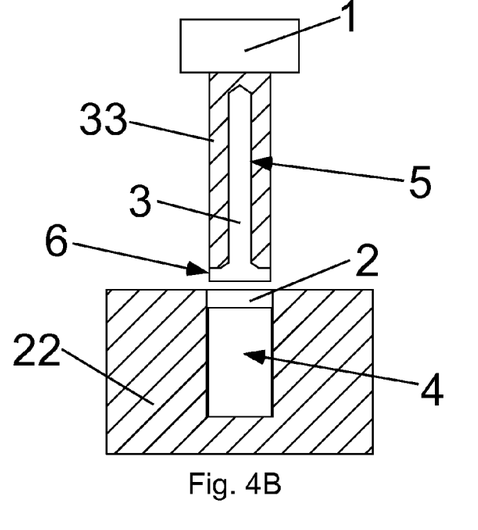

In an alternate, and fundamentally reversed arrangement depicted by FIG. 4B, the die cavity tooling 33, defining the die cavity 3 is operationally attached to the press ram 1. The actuation of the press ram 1 drives the die cavity tooling against the polymer slug 4, contained within the barrel 2, as defined by the barrel tooling 22.

Figure 8:
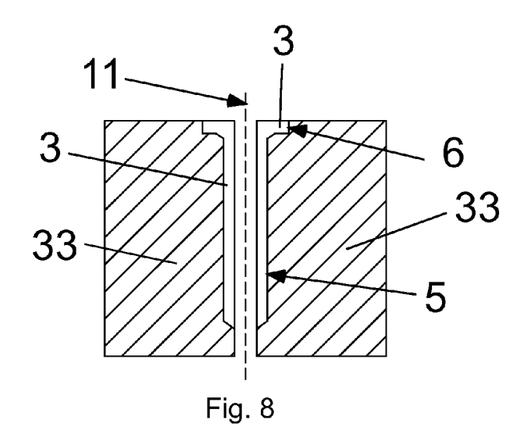
FIG. 8: Cross sectional depiction of a multi component die cavity tooling.

The barrel tooling 22 and die cavity tooling 33 shown in FIGS. 4A and 4B are individually depicted as single piece tooling, respectively forming the barrel geometry 2 and the die cavity geometry 3. It is recognized the particular construction of the barrel tooling 22 and die cavity tooling 33 may beneficially comprise multiple and separable components, particularly a two piece or multiple piece design in which it is preferable, but not necessary, for any parting line of tooling to run parallel with the longitudinal axis of the formed bone treating device or implant. FIG. 8 depicts a cross-sectional view of an exemplary separable, two-piece die cavity tooling 33 consisting of separable die cavity 3 with the parting line 11 of the tooling running parallel with the longitudinal axis of the formed device with device shank 5 and device head 6.

Referring again to the preferred embodiment depicted by FIG. 4A, but applicable to other described embodiments as well, the barrel 2 formed by the barrel tooling 22 should preferably mimic the outside geometry of the slug 4 to be placed within the barrel, though not necessary. Furthermore, the barrel tooling 22 and die cavity tooling 33 are preferably temperature controlled, incorporating a mechanism to provide heating and/or cooling (not shown). This is to allow proper heat transfer from the barrel tooling 22 to the slug 4. In operation, the slug 4 within the barrel 3 may be heated to a temperature between the glass transition temperature and melting temperature (as in a semi-crystalline polymer) of the material comprising the slug 4 or as applicable based on the material of the slug. The barrel 2 and barrel tooling 22 are heated to this desired temperature either prior to the slug 4 being placed in the barrel 2 or after the slug is placed in the barrel. Alternatively, the processing method for producing the final device also allows for the slug 4 to be heated to a temperature, again between the glass transition temperature and the melting point temperature of the slug material, prior to being placed in the barrel 2. In this case, the barrel may also be pre-heated.

Figure 5A:
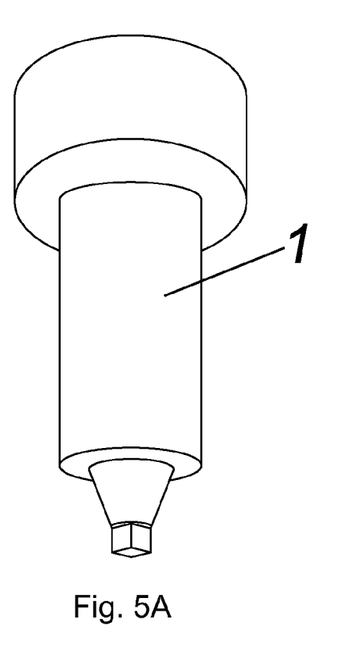
FIGS. 5A and 5B: Depictions of press ram component having complex external (5A) or internal (5B) geometry.
Figure 5B:
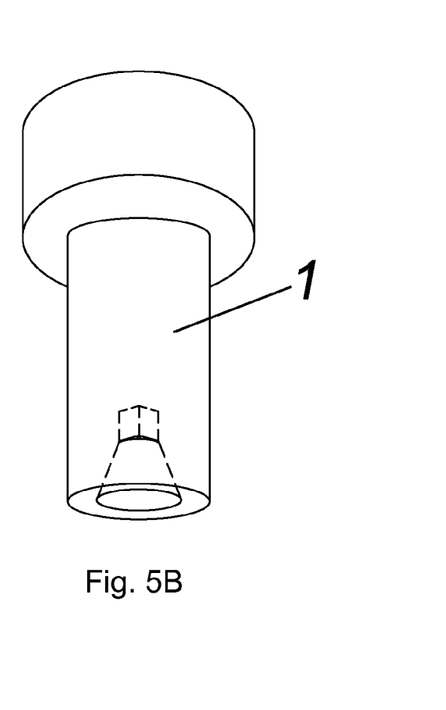

In an embodiment, a temperature gradient extending from the barrel 2 and the slug 4 to the die cavity 3 may be induced. The maximum and minimum temperature within this temperature gradient is preferably maintained between the glass transition temperature of the slug material and the melting temperature of the slug material. It is recognized there may be benefit in temperature set points that are (at least temporarily) somewhat higher or lower than the recorded glass transition and melting temperatures of the polymer, in order to account for heat transfer properties, or to intentionally derive a localized temperature variation. This temperature gradient may consist of a higher temperature at the barrel 2 and slug 4 location than at the die cavity 3 or with the gradient reversed, in which the highest temperature of the temperature gradient exists at the die cavity 3. In this embodiment, the surgical device or implant may have been processed by the method of the present invention at different temperatures along the length of the device. The temperature gradient when processing the material may influence the degree of orientation in the polymer, thereby increasing the mechanical properties along the longitudinal direction of the final surgical implant, tissue fixation device or bone treating device. Following heating of the slug 4 to the desired temperature and/or for the desired duration, the slug is driven by the actuation of press ram 1 into the die cavity 3 portion of the die cavity tooling 33. In a preferred embodiment, the geometry of the end of the press ram 1 in contact with the slug 4 is formed as a flat surface; however, the end may alternatively possess internal and external complex geometry. Complex geometry for the press ram 1 may include external complex geometry as shown in FIG. 5A, or internal complex geometry as shown in FIG. 5B. Either external or internal complex geometry may mimic geometry of the final device and cause the final device to be formed into the slug 4 during pressing. For example, the geometry shown in FIGS. 5A and 5B may form final bone treating device geometry that is used at the interface of the device and a surgical instrument (e.g. a driver of a fastener). Alternatively, the complex geometry shown in FIGS. 5A and 5B may inversely correspond to the complex geometry that is already present in the provided slug as previously discussed with reference to FIGS. 3A and 3B.

The ram 1 may or may not be pre-heated prior to pressing the slug 4. The ram may be driven by typical mechanical means known in the art (e.g., hydraulic, electric, rack & pinion etc.) However, the control and/or variability of speed, positioning, force and dwell may be varied to determine the mechanical and polymer alignment properties of the final part (i.e., the implantable device), and are essential in forming a final implant, tissue fixation device or bone treating device per the method of the present invention. In one embodiment, the actuation of the ram 1 forces the slug 4 into a dry cavity 3, or alternatively, the pressing of the slug may employ lubrication in order to facilitate the flow of the polymer slug 4 into the cavity 3.

In an alternate embodiment, the implant device may be formed by a similar process as described above, however relying on hydrostatic extrusion (not shown), wherein the actuation of the ram exerts pressure upon a fluid surrounding the slug in the barrel, forcing the slug into the die cavity. As is known in the art, one of the benefits of hydrostatic extrusion is the lubrication afforded by the non-compressible medium surrounding the slug. The device manufactured in the practice of the present invention features varied zones of polymer alignment. This zone variation occurs due to differences in how some areas of the slug 4 undergo deformation in conforming to the die cavity 3 as the ram exerts pressure, resulting in greater elongation and accordingly greater alignment in some areas, while other regions of the slug experience less deformation and therefore feature less alignment.

With reference again to FIG. 4A, the die cavity portion 3 of the die cavity tooling 33 consists of geometry in part or in full of the final bone treating device or implant to be formed. For example, where the implant to be manufactured is a tissue or bone fastener, the die cavity tooling 33 may consist of the shank diameter 5 of the bone fastener and also the head geometry 6 of the bone fastener device. The die cavity 3 consists of reduction in cross sections from one final part geometry to the next. For example, the die cavity depicted in FIG. 4A varies in cross section from the bone fastener head diameter 6 to the shank diameter 5 of the bone fastener form. The reduction in cross section affects the mechanical deformation and further orients the polymer molecules and molecular segments, thereby resulting in increased mechanical properties such as shear and bend resistance in the desired location. This occurs as the polymer slug material 4 that is driven into the shank diameter portion 5 of the die cavity 3 undergoes significantly more deformation and elongation in extending into the shank area, thereby creating significant alignment of the polymer molecules, when compared to the slug 4 material that is formed into the head portion 6 of the die cavity 3, where less deformation and elongation is required, resulting in significantly less reorientation of the polymer molecules. The desired location for increased mechanical properties such as shear and bend resistance, in this example, is the shank diameter 5 of a bone fastener.

In practice of the present invention, the polymer slug 4 is pressed into the die cavity 3 by the actuation of ram press 1, causing the slug to conform to, and completely fill, the die cavity, or alternatively to at least partially fill the die cavity. The cavity may be a substantially enclosed area defined by the die cavity tooling 33 having only one opening for the introduction and removal of the polymer material (as depicted by the die cavity 3 of FIG. 4A). In another embodiment, the die tooling may feature a second opening away from the ram press 1 to allow for the introduction of an ejection device or pin penetrating through the die cavity tooling, as can be seen in FIGS. 6 and 7.

Figure 6:
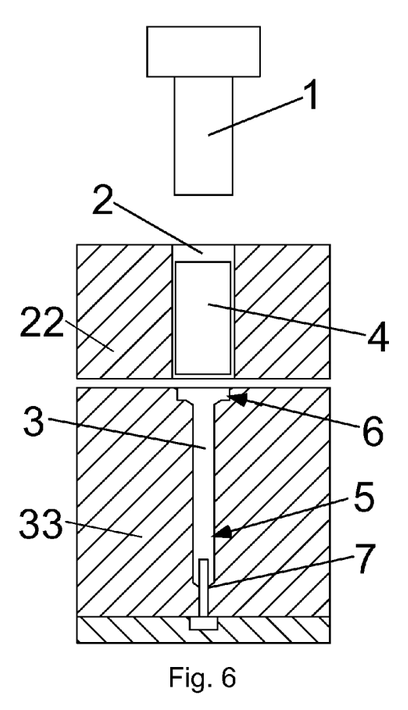
FIG. 6: Cross sectional depiction of die tooling arrangement having a hollow core forming ejector pin.

The ejection device of FIG. 6 features a pin 7 that extends through the die cavity tooling, and extends into the die cavity 3. In this embodiment, the ejection pin further serves to add to the geometry of the final device (e.g., by adding complex geometry as described above). In the example depicted in FIG. 6, the pin 7 may serve to create a slot or a hollow core in the device, created as the pressed polymer slug material surrounds the protruding pin or coring.

Figure 7:
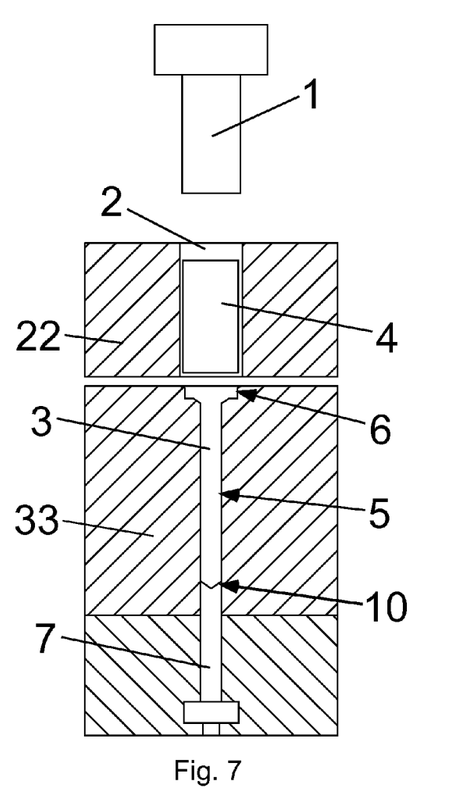
FIG. 7: Cross sectional depiction of die tooling arrangement having a solid tip forming ejector pin

In another embodiment, the ejection device depicted in FIG. 7 may serve as a temporary present die cavity closure, until ejection of the bone treating device is required. Ejection or removal of the bone treating device is preferably performed following proper cooling in the die cavity. The ejection device 7 may optionally consist of geometry 10 particular to the final bone treating device or implant. In the embodiment depicted by FIG. 7, the ejection pin 7 consists of geometry specific to the tip of a bone treating fastener.

Figure 9:
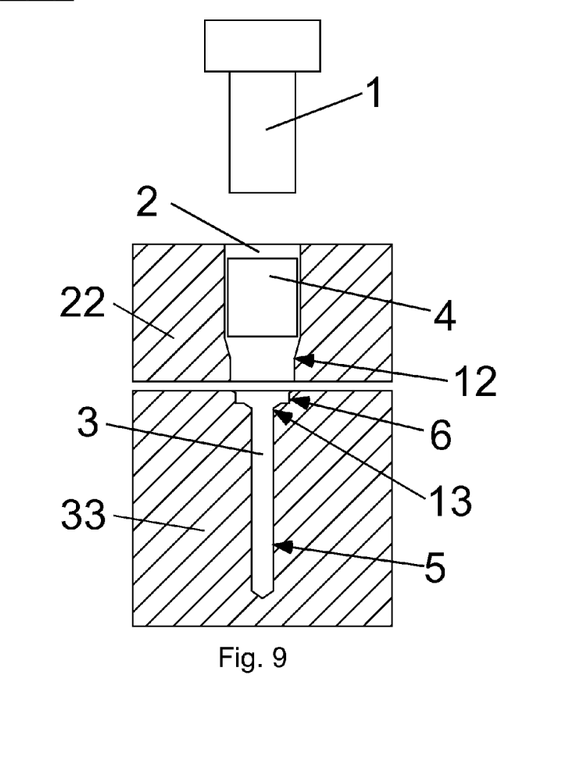
FIG. 9: Cross sectional depiction of die tooling arrangement having multiple reductions in cross section—one in the barrel component and one in the die cavity component.

The reduction or variation in cross-section and the inducing of zones of variable alignment through the pressing method described in the present invention does not need to only take place in the die cavity tooling 33 and die cavity 3, as has been previously described. In an alternative embodiment depicted by FIG. 9, the mechanical strengths of the shaped polymer material may further be increased by continuing to add step-downs in cross-section or increasing the number of variations in cross-section that further align the polymer molecular structure. This may be defined or described as double or multiple-pressing and may take place within either the barrel 2 of the barrel tooling 22, the cavity 3 of the cavity tooling 33, or both. FIG. 9 depicts an example of multiple reductions in cross section further aligning the polymeric molecular structure and obtaining a near net or final shape bone treating device or implant with varying zones or degrees of alignment. In FIG. 9, for example, but not limited to this location, the multiple reductions in cross section take place in both the barrel 2 of the barrel tooling 22 and also the die cavity 3 of the die cavity tooling 33. The locations of the reductions in cross-section and subsequent varying zones of alignment are shown by 12 and 13.

Alternatively, a way to increase the number of reductions in cross section and continue to increase the subsequent mechanical properties is to obtain an implant device through the method of the present invention and to repeat the method of the present invention one or more additional times. This is also an opportunity to not only continue to reduce the cross-section through the pressing operation and increase mechanical properties, but also to continue to add different geometry through the use of different tooling components (e.g., press ram 1, die cavity 3, etc.), the application of which may continue to accomplish a near net shape of the final bone treating device or implant and further reduce and/or eliminate subsequent machining or related processes.

After pressing per the method of the present invention, the device or implant may be cooled in the die components, either under pressure from the ram or another source, or alternatively the implant may be cooled after release of the pressure. Cooling may be controlled by providing for at least one cooling rate, and may vary locally within the die components, and/or temporally. The various cooling rates may be employed as required with respect to the material and design to be cooled.

The implant material, while still in the die cavity 3, may further be re-heated between the glass transition temperature (or thereabouts), and the melt temperature (or thereabouts), of the material and then the cooling process, either with or without pressure, and at one or multiple cooling rates, may be employed, as described above. This heating and/or cooling cycling may be employed as required with respect to the material, the design, and the advantages and/or disadvantages that such heating and/or cooling cycling may have on the final desired properties. For example, an amorphous material may require a different cooling rate(s) and/or a different temperature set point during a re-heating cycle than might a partially crystalline material to gain desired strength increases due to molecular aligning the respective polymer structure.

In a preferred embodiment, all stages in the manufacturing of the polymer implant device, from slug placement, ram pressing, slug forming within the die cavity, and ejection, are along a common longitudinal axis, which in the case of the simple cylindrical geometry shown in FIG. 1 is the axis of molecular orientation.

The above described operational processes and practices may be performed to form an implantable device with zones of variable alignment of the polymer structure, zones of varying cross-section and preferably, final part geometry of the implantable device.

Thus, since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A method for the manufacture of a device suitable for implantation in a living being, said method comprising the steps of:
   a. providing a polymer slug comprising a polymer material;
   b. providing a die cavity tooling and ram press, wherein said die cavity tooling defines a die shape having a plurality of zones of varying cross-section, and wherein said polymer slug has a polymeric molecular structure;
   c. placing said polymer slug between said ram press and a first die cavity tooling;

d. heating at least said polymer slug to a temperature in a range between the glass transition temperature and the melting temperature;
e. after said heating, actuating said ram press along an axis in order to apply pressure upon said polymer slug, thereby deforming said polymer slug and forcing said polymer slug to conform to said first die cavity shape, wherein said polymer slug is formed into a first device having zones of varying cross section;
f. removing said first device from said die cavity tooling;
g. placing said first device between a ram press and a second die cavity tooling whose die cavity comprises zones of cross-sections that are reduced relative to those of said first die cavity;
h. at a temperature in a range between the glass transition temperature and the melting temperature of the device, actuating said ram press along an axis in order to apply pressure upon said first device, thereby deforming said first device and forcing said polymer of said first device to conform to said second die cavity shape, wherein said polymer slug is formed into a second device having zones of varying cross section, wherein said deforming causes an alignment of said polymeric molecular structure, and further wherein at least one zone undergoes a greater degree of deformation and elongation than a different zone, thereby resulting in said first device being formed into a second device comprising zones of variable degrees of alignment of the polymer molecular structure, and zones of varying cross section, and specifically where a zone of smaller cross section has a greater degree of alignment of the polymer molecular structure than that polymer molecular structure in a zone of larger cross section;
and
i. removing said second device from said second die cavity tooling.

2. The method of claim 1, wherein said device has a length, and said method further comprises imposing a temperature gradient along said length.

3. The method of claim 1, wherein said polymer material is compounded with at least one plasticizer.

4. The method of claim 1, further comprising imposing a temperature gradient to at least one of said die cavity tooling and barrel.

5. The method of claim 1, wherein said polymer slug comprises a resorbable polymer.

6. The method of claim 5, wherein said resorbable polymer is selected from the group consisting of PLA, PGA, PGA/PLLA, DLPLA, and combinations thereof.

7. The method of claim 1, wherein said polymer slug provided further comprises additive materials.

8. The method of claim 7, wherein said additive materials are selected from the group consisting of ceramics, fibrous materials, particulate materials, biologically active agents, plasticizers and combinations thereof.

9. The method of claim 1, wherein at least one of said barrel and said die cavity tooling is temperature controlled.

10. The method of claim 1, wherein an end of said polymer slug comprises an ejection pin.

11. The method of claim 1, wherein said second die cavity adds different geometry to said second device relative to said first device.

* * * * *